US006127411A

United States Patent [19]
Riggs

[11] Patent Number: 6,127,411
[45] Date of Patent: Oct. 3, 2000

[54] SEED TREATMENT FUNGICIDES FOR CONTROL OF PLANT DISEASES

[75] Inventor: Jennifer Lynn Riggs, Plano, Tex.

[73] Assignee: Gustafson, Inc., Plano, Tex.

[21] Appl. No.: 09/340,104

[22] Filed: Jun. 25, 1999

Related U.S. Application Data

[62] Division of application No. 09/132,927, Sep. 12, 1998
[60] Provisional application No. 60/059,293, Sep. 18, 1997.

[51] Int. Cl.$^7$ .......... A01N 37/34; A01N 47/10
[52] U.S. Cl. .......... 514/479; 514/478; 514/491; 514/528
[58] Field of Search .......... 514/528, 491, 514/478, 479

[56] References Cited

U.S. PATENT DOCUMENTS

| | | | |
|---|---|---|---|
| 3,379,610 | 4/1968 | Channing | 167/32 |
| 3,905,995 | 9/1975 | Enoki | 260/309 |
| 3,957,847 | 5/1976 | Davidson | 260/465.4 |
| 4,742,079 | 5/1988 | Devoise-Lambert | 514/528 |
| 5,776,976 | 7/1998 | Dehne | 514/479 |

FOREIGN PATENT DOCUMENTS

| | | |
|---|---|---|
| 1470740 | 4/1977 | United Kingdom . |

OTHER PUBLICATIONS

Tomlin, The Pesticide Manual Incorporating the Agrochemicals Handbook, 10$^{th}$ Ed. (1995) pp. 257,258,987 & 988.

Samoucha et al, "Systemicity and persistance of cymoxanil in mixture with oxadixyl and mancozeb against *Phytophthora infestans* and *Plasmopara viticola*", Crop Protection 6(6): 393–398 (Dec. 1987).

Cohen et al, "Uptake, translocation and degradation of [$^{14}$C]cymoxanil in tomato plants", Crop Protection 12(4): 284–292 (Jun. 1993).

*Primary Examiner*—Allen J. Robinson
*Attorney, Agent, or Firm*—Sidley & Austin

[57] ABSTRACT

A method for combatting plant fungi in a plant, which comprises applying to the seeds or tubers of the plant, an effective amount of a fungicidal composition comprising a fungicidally effective amount of a 2-alkoxyiminoacetamide compound, optionally in admixture with one or both of an alkylene bis-dithiocarbamate complex salt and a thiophanate compound. Fungicidal compositions comprising a fungicidally effective amount of a 2-alkoxyimino-acetamide compound, an alkylene bis-dithiocarbamate complex salt, and a thiophanate compound, are also described.

15 Claims, No Drawings

SEED TREATMENT FUNGICIDES FOR CONTROL OF PLANT DISEASES

This application is a divisional U.S. application Ser. No. 09/132,927, filed Aug. 12, 1998, which claims the benefit of U.S. Provisional application Ser. No. 60/059,293, filed Sep. 18, 1997, entitled "SEED TREATMENT FUNGICIDES FOR CONTROL OF PLANT DISEASES."

FIELD OF THE INVENTION

This invention relates to a method for controlling fungus diseases in plants by applying to the seed or tuber a fungicidally effective amount of a 2-alkoxyimino-acetamide compound such as cymoxanil, optionally in admixture with one or more of an alkylene bis-dithiocarbamate complex salt such as mancozeb, and a thiophanate compound such as thiophanate-methyl. This invention also relates to a fungicidal composition comprising, in a fungicidally effective aggregate amount, a 2-alkoxyiminoacetamide compound, an alkylene bis-dithiocarbamate complex salt, and a thiophanate compound.

BACKGROUND OF THE INVENTION

Late Blight is the devastating disease that affected the Irish potato crop over 150 years ago. Today, however, the Late Blight fungus, *Phytophthora infestans,* is much different than its ancestors. New strains of *P. infestans* have evolved that are fungicide resistant and which are more aggressive with respect to pathogenicity on the potato tuber. As a result, the disease can now be introduced into potato fields by means of infected seed tubers more efficiently than in the past.

It is the purpose of this invention to provide a novel method for combatting plant fungi, particularly phytopathogenic fungi such as *Phytophthora infestans.* It is a purpose to provide a novel fungicidal composition useful for combatting plant fungi, particularly phytophogenic fungi such as *Phytophthora infestans.*

SUMMARY OF THE INVENTION

This invention relates to a method for combatting plant fungi in a plant, which comprises applying to the seeds or tubers of the plant, a fungicidally effective amount of:

a) a 2-alkoxyiminoacetamide compound of the formula:

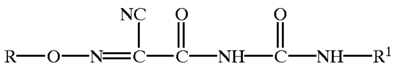

wherein R is methyl or ethyl and $R^1$ hydrogen, $C_1$–$C_4$ alkyl or allyl, preferably, $C_1$–$C_4$ alkyl, more preferably, methyl or ethyl; or b) the 2-alkoxyiminoacetamide compound in admixture with one or more compounds selected from the group consisting of:

i) an alkylene bis-dithiocarbamate complex salt of the formula:

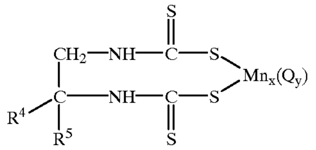

wherein $R^4$ and $R^5$ are each, independently, hydrogen or $C_1$–$C_6$ alkyl, preferably, hydrogen or $C_1$–$C_4$ alkyl, more preferably, hydrogen, methyl or ethyl; Q is Zn, Fe, or Cu, preferably, Zn; and the ratio of x to y is from about 3:1 to about 100:1, preferably, about 5:1 to about 20:1, more preferably, about 6:1 to about 10:1. and ii) a thiophanate compound of the formula:

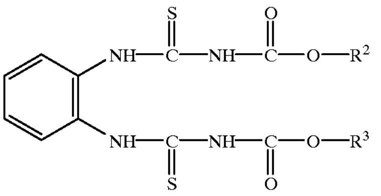

wherein $R^2$ and $R^3$ are each, independently, $C_1$–$C_6$ alkyl, preferably, $C_1$–$C_4$ alkyl, more preferably, methyl or ethyl.

This invention further relates to a fungicidal composition comprising:

a) a 2-alkoxyiminoacetamide compound of the formula:

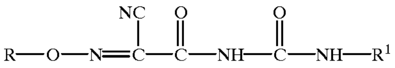

wherein R is methyl or ethyl and $R^1$ hydrogen, $C_1$–$C_4$ alkyl or allyl, preferably, $C_1$–$C_4$ alkyl, more preferably, methyl or ethyl;

b) an alkylene bis-dithiocarbamate complex salt of the formula:

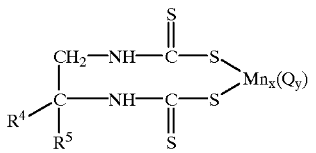

wherein $R^4$ and $R^5$ are each, independently, hydrogen or $C_1$–$C_6$ alkyl, preferably, hydrogen or $C_1$–$C_4$ alkyl, more preferably, hydrogen, methyl or ethyl; Q is Zn, Fe, or Cu, preferably, Zn; and the ratio of x to y is from about 3:1 to about 100:1, preferably, about 5:1 to about 20:1, more preferably, about 6:1 to about 10:1; and c) a thiophanate compound of the formula:

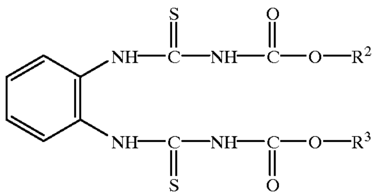

wherein $R^2$ and $R^3$ are each, independently, $C_1$–$C_6$ alkyl, preferably, $C_1$–$C_4$ alkyl, more preferably, methyl or ethyl, in an effective aggregate amount.

DESCRIPTION OF THE INVENTION

The 2-alkoxyiminoacetamide compounds, alkylene bis-dithiocarbamate complex salts, and thiophanate compounds useful in the method and composition of this invention, are known in the art, as are methods for their preparation. See, e.g., U.S. Pat. Nos. 3,957,847; 3,379,610; and 5,571,443, respectively.

The method and composition of this invention are particularly suitable for use against *Phytophthora infestans* on or in potato plants and tubers.

The composition of this invention and the compounds useful in the method of this invention can be formulated in conventional ways. Examples of useful formulations include slurries, solid seed coatings, soaks, dusts on the surface of the seed or tuber, solutions, suspensions, emulsions, wettable powders, emulsifiable concentrates, and the like. The formulations, in general, comprise about 1% to 99% by weight of active ingredient. The formulations can additionally comprise additional additives such as surfactants, solid or liquid diluents, pigments, thickeners, and the like. The method of application of the formulations to the seeds or tubers can vary depending, e.g., on the compounds and/or the formulation used.

In general, the seed or tuber should be treated with about 50 to about 1200 ppm, preferably between about 300 to about 900 ppm, most preferably, about 700 ppm, per 100 pounds ("cwt") of seed or tuber, of the composition of this invention or of the compounds useful in the method of this invention.

This invention preferably relates to a method for combatting plant fungi in a plant, which comprises applying to the seeds or tubers of the plant, an effective amount of a fungicidal composition comprising a fungicidally effective amount of:

a) cymoxanil; or b) cymoxanil in admixture with one or more of the group consisting of mancozeb and thiophanate-methyl.

This invention further preferably relates to a fungicidal composition comprising cymoxanil, mancozeb and thiophanate-methyl, in an effective aggregate amount.

Cymoxanil, mancozeb and thiophanate-methyl are all known compounds.

Cymoxanil (a foliar fungicide sold under the trademarks CURZATE and DPX-3217) is 2-cyano-N-[(ethylamino) carbonyl]-2-(methoxyimino)-acetamide.

Mancozeb (a fungicide sold under the trademarks MANZATE-200 and DITHANE M-45) is a mixture of [[1,2-ethanediylbis-(carbamodithioato)](2-)]manganese and [[1,2-ethanediylbis(carbamothioato)](2)-]zinc.

Thiophanate-methyl (a systemic fungicide sold under the trademarks TOPSIN M and NF-44) is dimethyl[1,2-phenylene-bis-(iminocarbono-thioyl)-bis-[carbamate].

In the method of this invention wherein cymoxanil is admixed with thiophanate-methyl, in general, satisfactory results can be obtained when the weight ratio of cymoxanil:thiophanate-methyl is from about 1:3 to 3:1, preferably 1:2 to 2:1, and more preferably, 1:1.5 to 1.5:1.

In the method of this invention wherein cymoxanil is admixed with mancozeb, in general, satisfactory results can be obtained when the weight ratio of cymoxanil:mancozeb is from about 1:16 to 3:1, preferably 1:8 to 2:1, and more preferably, 1:3 to 1.5:1.

In the method of this invention wherein cymoxanil, mancozeb and thiophanate-methyl are admixed, in general, satisfactory results can be obtained when the weight ratio of cymoxanil:mancozeb:thiophanate-methyl is from about 3:1:1 to about 1:16:6, preferably, about 1.5:1:1 to about 1:8:3.

Similarly, in the composition of this invention, in general, satisfactory results can be obtained when the weight ratio of cymoxanil:mancozeb:thiophanate-methyl is from about 3:1:1 to about 1:16:6, preferably, about 1.5:1:1 to about 1:8:3.

The formulations can comprise from 0 to about 20% of an agriculturally acceptable surfactant such as wetting and dispersing agents, e.g., the condensation product of formaldehyde with naphthalene sulphonate, an alkylarylsulphonate, a lignin sulphonate, a fatty sulphate, an ethoxylated alkylphenol and an ethoxylated fatty alcohol. The formulations can additionally comprise from about 10 to about 99% of an agriculturally acceptable solid or liquid diluent, including carriers, such as talc, zeolites, Alder bark, kaolin, diatomaceous earth, mineral oil, water, and the like.

The following examples are provided to illustrate the present invention.

EXAMPLES

Example 1

(A) A potato dust inert system (PDIS) was prepared by blending the following three inert diluents in a ribbon blender: talc (Cyprus BT-200) (48.39% w/w), zeolite (16.12% w/w) , and Alder bark (35.49% w/w).

The dusts listed in Table 1 below were prepared by blending PDIS and the compounds at the concentrations indicated in a ribbon blender and were evaluated for activity against *P. infestans* at the rate of application of active ingredient indicated.

TABLE 1

| Dust No. | Compound | Percent (w/w) | Percent PDIS (w/w) | Rate of Application (ppm/cwt[1]) |
|---|---|---|---|---|
| 1 | Cymoxanil | 10.5 | 89.5 | 500 |
| 2 | Cymoxanil | 5.3 | 91.5 | 250 |
| | Topsin[2] | 3.2 | | 150 |
| 3 | Dimethomorph[3] | 10.5 | 89.5 | 500 |
| 4 | Dimethomorph | 5.3 | 91.5 | 250 |
| | Topsin | 3.2 | | 150 |
| 5 | Propamocarb[4] | 10.5 | 89.5 | 500 |
| 6 | Propamocarb | 5.3 | 91.5 | 250 |
| | Topsin | 3.2 | | 150 |
| 7 | Topsin | 5.3 | 94.7 | 250 |

TABLE 1-continued

| Dust No. | Compound | Percent (w/w) | Percent PDIS (w/w) | Rate of Application (ppm/cwt[1]) |
|---|---|---|---|---|
| 8 | Topsin | 2.6 | 89.9 | 250 |
| | Mancozeb | 7.5 | | 600 |

[1]parts per million per hundred lbs. of seed (tuber)
[2]thiophanate-methyl
[3](E,Z) 4-[3-(4-chlorophenyl)-3-(3,4-dimethoxyphenyl) acryloyl]morpholine
[4]Propyl [3-(dimethylamino)propyl]carbamate (B) The in-vitro screening procedure was conducted as follows:

Potato tubers were removed from 5° C. storage and allowed to come to room temperature. The tubers were then washed with tap water and sterilized in 5% commercial bleach (Clorox) for 10 minutes. The tubers were then rinsed in sterile distilled water and dried.

*Phytophthora infestans* was grown on agar plates at 18° C. for 10–14 days. 20 ml. of 5° C. sterile distilled water were then added to each plate. The agar was then agitated or cut into smaller sections and placed at 10–12 ° C. for 2 hours to release zoospores.

Tubers were cut into uniform sized slices (1 cm thick). Each dust was applied to 20 slices at 0.5 lb/cwt. Two sets of 20 potato slices were left untreated with dust and used as controls. Each dusted potato slice was then placed on sterile moistened filter paper in a sterile petri dish.

A zoospore suspension was quantified to a concentration of 20,000 spores/ml. 100 $\mu$l of this spore suspension was then applied to a sterile filter paper disk. One such treated disk was placed in the center of each potato slice. One set of 20 undusted potato slices were not inoculated and used as a sterile control.

Each potato slice was then placed in the dark at 18° C. for 7 days. After the 7 days, the disease state of each potato slice was assessed.

In Table 2 below, growth and sporulation of *P. infestans* for each potato slice was rated on a plus (+) or minus (–) scale. A minus indicates no growth of the *P. infestans* whereas a plus indicates growth. Growth was measured as minimal (+), good (++), or good and sporulation (+++)

TABLE 2

GROWTH AND SPORULATION OF *P. INFESTANS*

| Dust No. | Growth |
|---|---|
| 1 | – |
| 2 | – |
| 3 | – |
| 4 | – |
| 5 | +++ |
| 6 | ++ |
| 7 | + |
| 8 | – |
| Untreated | +++ |
| Sterile | – |

Example 2

(A) Dusts were prepared as described in Example 1 above.

(B) The in-vivo screening procedure was conducted as follows:

Potato tubers were removed from 5° C. storage and allowed to come to room temperature. The tubers were then washed with tap water and sterilized in 5% commercial bleach (Clorox) for 10 minutes. The tubers were then rinsed in sterile distilled water and dried.

*Phytophthora infestans* was grown on agar plates at 18° C. for 10–14 days. 20 ml. of 5° C. sterile distilled water were then added to each plate. The agar was then agitated or cut into smaller sections and placed at 10–12° C. for 2 hours to release zoospores. A zoospore suspension was quantified to a concentration of 20,000 spores/ml.

Small punctures were made in the tubers with a sterile needle and the punctured tubers were then dipped into the suspension of *P. infestans* zoospores. The tubers were then incubated at 15° C. with 95% relative humidity for 7–10 days. After the incubation the tubers were then cut into 2–4 oz. pieces. Each dust was applied to 15 pieces at 0.5 lb/cwt or according to manufacturer's directions. One set of 15 pieces was left untreated and used as a control.

Potatoes not dipped in the zoospores were also cut into 2–4 oz. pieces and one set of 15 uninoculated potato pieces was used as a sterile control.

The potato pieces were then placed in sandy soil and incubated at 17° C. days and 13° C. nights for 32 days. Growth after emergence was monitored for 14–28 days. Disease symptoms were visually rated. Stem/leaf tissue was assayed for *P. infestans* on appropriate media.

Finally, potato seed pieces were then removed and cut in half and disease presence was visually assessed.

The results of this test are presented below in Tables 3 and 4.

TABLE 3

Germination and Emergence Results

| Dust No. | Emergence (%) Day 14 | Germination (%) Day 32 |
|---|---|---|
| 1 | 33.3 | 100 |
| 2 | 33.3 | 100 |
| 3 | 26.7 | 80 |
| 4 | 33.3 | 53.3 |
| 6 | 20 | 40 |
| 8 | 6.7 | 6.7 |
| Untreated | 20 | 13.3 |
| Sterile | 33.3 | 100 |

TABLE 4

TUBER AND STEM HEALTH

| Dust No. | A[1] (%) | B[2] (%) | C[3] (%) | D[4] (%) |
|---|---|---|---|---|
| 1 | 0 | 0 | 26.7 | 73.3 |
| 2 | 0 | 0 | 0 | 100 |
| 3 | 20 | 26.7 | 53.3 | 0 |
| 4 | 40 | 13.3 | 40 | 0 |
| 6 | 60 | 20 | 20 | 0 |
| 8 | 93.3 | 6.7 | 0 | 0 |
| Untreated | 86.7 | 13.3 | 0 | 0 |
| Sterile | 0 | 0 | 0 | 100 |

[1]Blighted tuber; No emergence
[2]Blighted tuber; Small-sized infected stems
[3]Blighted tuber; Average-sized infected stems
[4]Clean tubers; Healthy uninfected stems

Example 3

The following new dusts in Table 5 were prepared as described in Example 1.

TABLE 5

| Dust No. | Compound | Percent (w/w) | Percent PDIS (w/w) | Rate of Application (ppm/cwt) |
|---|---|---|---|---|
| 9 | Cymoxanil | 5.3 | 94.7 | 250 |
| 10 | Cymoxanil | 2.1 | 94.7 | 100 |
| | Topsin[2] | 3.2 | | 150 |
| 11 | Cymoxanil | 4.2 | 92.6 | 200 |
| | Topsin | 3.2 | | 150 |
| 12 | Cymoxanil | 2.1 | 92.2 | 100 |
| | Mancozeb | 2.5 | | 100 |
| | Topsin | 3.2 | | 150 |
| 13 | Topsin | 5.2 | 87.3 | 500 |
| | Mancozeb | 7.5 | | 600 |

These dusts were tested using the procedure described in Example 2 above. The results of this testing is shown in Table 6 below.

TABLE 6

EMERGENCE AND TUBER AND STEM HEALTH

| | Emergence (%) | | | Infection (%) | |
|---|---|---|---|---|---|
| Dust No. | Day 15 | Day 23 | Day 35 | Tubers | Stems |
| 9 | 0 | 20 | 80 | 20 | 0 |
| 10 | 0 | 0 | 60 | 40 | 33.3 |
| 11 | 0 | 20 | 100 | 40 | 33.3 |
| 12 | 20 | 80 | 100 | 0 | 0 |
| 13 | 0 | 0 | 0 | 100 | no stems |
| Untreated | 0 | 0 | 0 | 100 | no stems |
| Sterile | 0 | 100 | 100 | 0 | 0 |

Example 4

The following dusts in Table 7 were prepared as described in Example 1.

TABLE 7

| Dust No. | Compound | Percent (w/w) | Percent PDIS (w/w) | Rate of Application (ppm/cwt) |
|---|---|---|---|---|
| 14 | Mancozeb(80%) | 10.0 | 90.0 | 400 |
| 15 | Cymoxanil(96%) | 2.1 | 97.9 | 100 |
| 16 | Cymoxanil(96%) | 2.1 | 90.9 | 100 |
| | Mancozeb(80%) | 7.5 | | 300 |
| 17 | Topsin(95%) | 3.2 | 92.8 | 150 |
| | Cymoxanil(50%) | 4.0 | | 100 |
| 18 | Topsin(95%) | 3.2 | 84.7 | 150 |
| | Mancozeb(80%) | 10.0 | | 400 |
| | Cymoxanil(96%) | 2.1 | | 100 |
| 19 | Topsin(95%) | 3.2 | 87.3 | 150 |
| | Mancozeb(80%) | 7.5 | | 300 |
| | Cymoxanil(96%) | 2.1 | | 100 |

These dusts (as well as Dust Nos. 7 and 8) were tested using the procedure described in Example 2 above using Russet Burbank tubers. The results of this testing (10 replications/treatment) are shown in Table 8 below.

TABLE 8

EMERGENCE AND STEM HEALTH

| | Emergence (%) | | Infection (%) |
|---|---|---|---|
| Dust No. | Day 14 | Day 28 | Stems |
| 7 | 0 | 0 | no stems |
| 8 | 10 | 10 | 100 |
| 14 | 0 | 10 | 100 |
| 15 | 30 | 40 | 25 |
| 16 | 20 | 40 | 0 |
| 17 | 10 | 30 | 33 |
| 18 | 30 | 40 | 0 |
| Untreated | 0 | 0 | no stems |
| Sterile | 60 | 100 | 0 |

Example 5

The dusts prepared in Example 4 above (as well as Dust Nos. 7 and 8) were tested using the procedure described in Example 2 above using Red Nordland tubers. The results of this testing (7 replications/treatment) are shown in Table 9 below.

TABLE 9

EMERGENCE AND STEM HEALTH

| | Emergence (%) | | Infection (%) |
|---|---|---|---|
| Dust No. | Day 10 | Day 38 | Stems |
| 7 | 0 | 0 | no stems |
| 8 | 14.3 | 14.3 | 100 |
| 14 | 0 | 0 | no stems |
| 15 | 85.7 | 100 | 14 |
| 16 | 57.1 | 85.7 | 0 |
| 17 | 42.9 | 85.7 | 14 |
| 18 | 71.4 | 100 | 0 |
| Untreated | 0 | 0 | no stems |
| Sterile | 57.1 | 100 | 0 |

Example 6

Shepody potato tubers were contaminated/inoculated with *Phytophthora infestans* and set aside ("source tubers"). After two weeks, one (1) source tuber was cut into quarters through the diseased area with a cutting knife. Without cleaning or changing the knife, five (5) uninoculated Shepody potato tubers were then cut into quarters. This process (1 source tuber/5 uninfected tubers) was repeated to provide enough tubers for 30 replications per treatment (Table 10 below).

The cut tubers (source and uninoculated) were weighed and the appropriate amount of each dust listed in Table 10 below was applied to the tubers by placing the tubers in a double paper bag with dust and then shaking the bag.

The treated tubers were then placed in an unsealed plastic bag (one bag per treatment) and incubated at 10° C., 80–90% RH, for two (2) weeks. After two (2) weeks, the bagged tubers were removed from the 10° C., 80–90% RH environment. The bags were then rolled or shaken to simulate movement from storage to planting areas. The tubers were removed and the spread of *P. infestans* was determined—% infected tubers. The tubers were warmed to room temperature and planted. The source tubers were not planted. Emergence and infection data were obtained as described above in Example 2 (30 replications/treatment).

The results of this test are listed below in Table 10.

TABLE 10

EMERGENCE AND TUBER AND STEM HEALTH

| Dust No. | Emergence (%) Day 6 | Emergence (%) Day 20 | Infection (%) Tubers (Before planting) | Infection (%) Stems |
|---|---|---|---|---|
| 7 | 20 | 86.7 | 60 | 40 |
| 8 | 26.7 | 80 | 40 | 20 |
| 14 | 20 | 83.3 | 20 | 10 |
| 15 | 30 | 100 | 20 | 0 |
| 17 | 40 | 93.3 | 40 | 0 |
| 18 | 56.7 | 100 | 30 | 0 |
| 19 | 20 | 100 | 30 | 0 |
| Untreated | 16.7 | 70 | 90 | 40 |

Example 7

The procedure described above in Example 6 was repeated using Red Nordland potato tubers. The results of this test are present below in Table 11.

TABLE 11

EMERGENCE AND TUBER AND STEM HEALTH

| Dust No. | Emergence (%) Day 8 | Emergence (%) Day 25 | Infection (%) Tubers (Before planting) | Infection (%) Stems |
|---|---|---|---|---|
| 7 | 20 | 83.3 | 47.5 | 33 |
| 8 | 20 | 83.3 | 52.5 | 33 |
| 14 | 30 | 70 | 52.5 | 0 |
| 15 | 26.7 | 90 | 50 | 0 |
| 17 | 26.7 | 96.7 | 45 | 0 |
| 18 | 36.7 | 100 | 45 | 0 |
| 19 | 20 | 96.7 | 35 | 0 |
| Untreated | 10 | 20 | 60 | 33 |
| Sterile | 36.7 | 100 | 0 | 0 |

The results in Tables 10 and 11 demonstrate that tubers contaminated with *P. infestans* spread from a contaminated seed source through the cutting and handling of the tubers prior to treatment and planting, still produced plants that were disease free when the tubers were treated in accordance with the present invention prior to planting.

What is claimed is:

1. A fungicidal composition comprising an enhanced fungicidally effective amounts of a) a 2-alkoxyiminoacetamide compound of the formula:

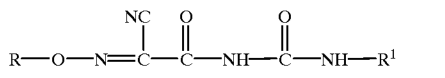

wherein R is methyl or ethyl and $R^1$ is hydrogen, $C_1$–$C_4$ alkyl or allyl;

b) an alkylene bis-dithiocarbamate complex salt compound of the formula:

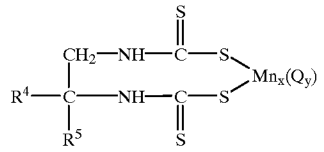

wherein $R^4$ and $R^5$ are each, independently, hydrogen or $C_1$–$C_6$ alkyl; Q is Zn, Fe, or Cu; and the ratio of x to y is from about 3:1 to about 100:1; and c) a thiophanate compound of the formula:

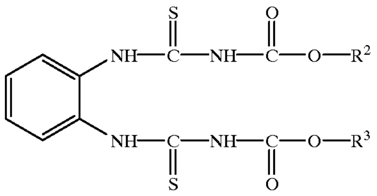

wherein $R^2$ and $R^3$ are each, independently, $C_1$–$C_6$ alkyl.

2. A composition as recited in claim 1 wherein $R^1$ and $R^2$, and $R^3$ are each, independently, $C_1$–$C_4$ alkyl, and $R^4$ and $R^5$ are each, independently, hydrogen or $C_1$–$C_4$ alkyl.

3. A composition as recited in claim 2 wherein $R^1$, $R^2$, and $R^3$ are each, independently, methyl or ethyl, and $R^4$ and $R^5$ are each, independently, hydrogen, methyl or ethyl.

4. A composition as recited in claim 3 wherein Q is Zn and the ratio of x to y is from about 5:1 to about 20:1.

5. A composition as recited in claim 4 wherein the ratio of x to y is from about 6:1 to about 10:1.

6. A composition as recited in claim 5 wherein the 2-alkoxyiminoacetamide compound is cymoxanil; the alkylene bis-dithiocarbamate complex salt compound is mancozeb; and the thiophanate compound is thiophanate-methyl.

7. A composition of claim 1 wherein said 2-alkoxyiminoacetamide compound, said alkylene bis-dithiocarbamate complex salt compound and said thiophanate compound are present in a ratio of from about 3:1:1 to about 1:16:6.

8. A composition of claim 1 wherein said 2-alkoxyiminoacetamide compound, said alkylene bis-dithiocarbamate complex salt compound and said thiophanate compound are present in a ratio of from about 1.5:1:1 to about 1:8:3.

9. A composition of claim 1 wherein said 2-alkoxyiminoacetamide compound, said alkylene bis-dithiocarbamate complex salt compound and said thiophanate compound are present in a ratio of about 2.1:10:3.2.

10. A composition of claim 5 wherein said 2-alkoxyiminoacetamide compound, said alkylene bis-dithiocarbamate complex salt compound and said thiophanate compound are present in a ratio of from about 3:1:1 to about 1:16:6.

11. A composition of claim 5 wherein said 2-alkoxyiminoacetamide compound, said alkylene bis-dithiocarbamate complex salt compound and said thiophanate compound are present in a ratio of from about 1.5:1:1 to about 1:8:3.

12. A composition of claim 3 wherein said 2-alkoxyiminoacetamide compound, said alkylene bis-dithiocarbamate complex salt compound and said thiophanate compound are present in a ratio of from about 3:1:1 to about 1:16:6.

13. A composition of claim 3 wherein said 2-alkoxyiminoacetamide compound, said alkylene bis-dithiocarbamate complex salt compound and said thiophanate compound are present in a ratio of from about 1.5:1:1 to about 1:8:3.

14. A composition of claim 6 wherein said cymoxanil, said mancozeb, and said thiophanate-methyl are present in a ratio of from about 3:1:1 to about 1:16:6.

15. A composition of claim 6 wherein said cymoxanil, said mancozeb, and said thiophanate-methyl are present in a ratio of from about 1.5:1:1 to about 1:8:3.

* * * * *

UNITED STATES PATENT AND TRADEMARK OFFICE
CERTIFICATE OF CORRECTION

PATENT NO. : 6,127,411
DATED : October 3, 2000
INVENTOR(S) : Jennifer Lynn Riggs It is certified that error appears in the above-identified patent and that said Letters Patent is hereby corrected as shown below:

On the Title Page,
Insert --The term of this patent is terminally disclaimed so that its term does not extend beyond the term of the patent issuing from pending allowed U.S. Application Serial No. 09/132,927, filed August 12, 1998.--.

Item [62], after "09/132,927,", delete "Sep." and insert --Aug.--.

Item [56], References Cited, U.S. PATENT DOCUMENTS, the fourth line, after "514/528", insert --5,007,953, 6/1991, Chollet, 71/77--.

Item [56], References Cited, OTHER PUBLICATIONS, after "Cohen et al, "Uptake, translocation, and degradation of [$^{14}$C] cymoxanil in tomato plants" , Crop Protection 12 (4) : 284-292 (Jun. 1993)." , insert
--Glasshouse Evaluation of Fungicides For The Control Of Sunflower Downy Mildew *Plasmopara-Halstedii*", Oros G. and Viranyi, F., Biological Abstract, Vol. 84, Abstract No. 8605, Annals of Applied Biology, 110 (1) , 1987, pp. 53-64--;

--"Field Control of Potato Late Blight by Synergistic Fungicidal Mixtures", Samoucha, Yair and Cohen, Yigal, Chemical Abstract, Vol. 111, No. 25, December 18, 1989, Plant Dis., 73(9), 1989, pp. 751-743--.

--"Efficacy Over Time Of Cymoxanil Mixtures In Controlling Late Blight in Potatoes Incited By A Phenylamide-Resistant Isolate of *Phytophthora Infestans*", Samoucha, Y, Levy, R.S., and Cohen, Y., Chemical Abstract, Vol. 109, No. 13, September 26, 1988, Crop Prot., 7 (3), 1988, pp. 210-215--.

--Synergistic Interactions of Cymoxanil Mixtures In The Control Of Metalaxyl-Resistant *Phytophthora Infestans* Of Potato", Samoucha, Yair and Cohen, Yigal, Chemical Abstract, Vol. 109, No. 15, October 10, 1988, Phytopathology, 78 (6), 1988, pp. 636-640--.

UNITED STATES PATENT AND TRADEMARK OFFICE

CERTIFICATE OF CORRECTION

PATENT NO. : 6,127,411
DATED : October 3, 2000
INVENTOR(S) : Jennifer Lynn Riggs It is certified that error appears in the above-identified patent and that said Letters Patent is hereby corrected as shown below:

--Composition For Fighting Tuber and Tuber Bulb Rot - Containing Mancozeb Combined With Benomil, Methyl Thiophanate Or Thia – Bendazole And Tetracycline Or Chloramphenicol", Alexandri, A. , Baicu, T. , Bftlan, E., and Plamadeala, B., Database WPI, Derwent Publications, Ltd., London, GB, AN 83-762767--.

Column 9,
Line 55, Claim 1, after "of ", insert --:--.

Signed and Sealed this

Nineteenth Day of June, 2001

Nicholas P. Godici

Attest:

NICHOLAS P. GODICI

*Attesting Officer* *Acting Director of the United States Patent and Trademark Office*